(12) United States Patent
Dijkstra

(10) Patent No.: US 11,602,640 B2
(45) Date of Patent: Mar. 14, 2023

(54) IRRADIATION DEVICE WITH ADJUSTABLE BEAM ANGLE

(71) Applicant: Light Tree Ventures Holding B.V., Rijswijk (NL)

(72) Inventor: Alain Dijkstra, Amstelveen (NL)

( * ) Notice: Subject to any disclaimer, the term of this patent is extended or adjusted under 35 U.S.C. 154(b) by 33 days.

(21) Appl. No.: 16/875,991

(22) Filed: May 16, 2020

(65) Prior Publication Data
US 2021/0353953 A1    Nov. 18, 2021

(51) Int. Cl.
*A61N 5/06* (2006.01)

(52) U.S. Cl.
CPC ........ *A61N 5/06* (2013.01); *A61N 2005/0632* (2013.01); *A61N 2005/0652* (2013.01); *A61N 2005/0653* (2013.01); *A61N 2005/0659* (2013.01); *A61N 2005/0661* (2013.01); *A61N 2005/0662* (2013.01)

(58) Field of Classification Search
CPC ....................................................... A61N 5/06
See application file for complete search history.

(56) References Cited

U.S. PATENT DOCUMENTS

| | | | |
|---|---|---|---|
| 8,415,879 | B2 | 4/2013 | Lowenthal et al. |
| 8,809,126 | B2 | 8/2014 | Lowenthal et al. |
| 8,846,457 | B2 | 9/2014 | Lowenthal et al. |
| 8,852,467 | B2 | 10/2014 | Lowenthal et al. |
| 8,877,101 | B2 | 11/2014 | Lowenthal et al. |
| 9,018,833 | B2 | 4/2015 | Lowenthal et al. |
| 2002/0161418 | A1* | 10/2002 | Wilkens ................ H01J 61/125 607/90 |
| 2005/0105690 | A1* | 5/2005 | Pau ........................ H01J 35/00 378/145 |

(Continued)

FOREIGN PATENT DOCUMENTS

| | | | |
|---|---|---|---|
| CN | 202791418 U | * | 3/2013 |
| CN | 202791418 U | | 3/2013 |

(Continued)

OTHER PUBLICATIONS

Egger, J. Use of Fresnel lenses in optical systems: some advantages and limitations. Proc. SPIE 0193, Optical Systems in Engineering I, (Nov. 29, 1979); https://doi.org/10.1117/12.957873 (Year: 1979).*

*Primary Examiner* — Mallika D Fairchild
*Assistant Examiner* — Shreya Anjaria
(74) *Attorney, Agent, or Firm* — Willie Jacques; Emanus, LLC

(57) ABSTRACT

An irradiation device capable of emitting electromagnetic radiation at variable beam angles, comprises, a housing assembly including a longitudinal shell, the longitudinal shell having a first end and a second end, a first end cap assembly provided at the first end of the longitudinal shell, and a second end cap assembly provided at the second end of the longitudinal shell. Further, the irradiation device comprises a rotate and lock mechanism adapted to allow rotational adjustment of the longitudinal shell, a plurality of lenses provided along with the longitudinal shell, wherein each one of the plurality of lenses has a distinct set of optical characteristics when compared with other lenses of the plurality of lenses and a radiation source configured to emit electromagnetic radiation, provided within the longitudinal shell.

6 Claims, 10 Drawing Sheets

(56) References Cited

U.S. PATENT DOCUMENTS

2016/0129279 A1* 5/2016 Ferolito .............. A61N 5/0616
607/94
2016/0367833 A1* 12/2016 Salinas .................... A61F 7/10
2020/0315907 A1* 10/2020 Dijkstra .................. A61H 1/00

FOREIGN PATENT DOCUMENTS

| CN | 204805995 U | * 11/2015 |
| CN | 204805995 U | 11/2015 |
| CN | 207065451 U | 3/2018 |

* cited by examiner

IRRADIATION DEVICE WITH ADJUSTABLE BEAM ANGLE

TECHNICAL FIELD

The present invention relates generally to devices capable of generating and disseminating radiation in Ultra-Violet (UV), visible light, and infrared frequencies of the electromagnetic spectrum. More specifically, the present invention relates to irradiation devices capable of achieving emissions of the radiations with variable beam angles.

BACKGROUND ART

Irradiation devices can be used for several applications based on the wavelengths (λ) and frequencies (ν) at which such devices emit electromagnetic radiation. They can be used in medical imaging when configured to emit X-Rays (λ varying between 0.1 to 10 nm), for cosmetic and non-invasive therapeutic applications when configured for Infrared radiation (λ varying between 700 nm to 1 mm) or red light (λ varying between 625 to 740 nm) or blue light (λ varying between 450 to 485 nm) or even some cases UV radiation (λ varying between 10 to 400 nm). Also, they can be used for spatial lighting purposes when configured to emit wide spectrum visible light (λ varying between 380 to 740 nm). Different types of irradiation devices are available in the market e.g. lasers, incandescent lamps, compact fluorescent lamps, halogen lamps, Light Emitting Diodes (LEDs) based lamps, fluorescent tube lights, and neon lamps, etc.

When it comes to the discussion of practical applications of such irradiation devices, the inverse square law in terms of electromagnetic radiation states that intensity of the radiation at a point, in the region being irradiated, decreases by the order of the square of the distance of the point from the source of the radiation. As a consequence, the more such a point is distant from the radiation source, the lesser would be the intensity of the radiation falling on that point. It is to be further noted that, while an ideal radiation source would emit radiations equally in all directions around the source, however, due to constructional constraints and, in many cases, due to demands of the applications, most of the irradiation devices emit radiation in with a conical profile. Therefore, when a plane is being irradiated by an irradiation device, a point in the plane just opposite of the irradiation device receives greater intensity, as compared to a point that subtends an angle at the irradiation device as the radiation reaching that point is traveling a longer distance when compared to the point that is just opposite the irradiation device.

It would be intuitive to imagine, however, that since the emitted radiation is following a conical profile there will be two such points symmetrically located about the point just opposite of the irradiation device. The angle subtended at the irradiation device, by two such points where the intensity of the radiation received is half of the intensity received by the point just opposite of the irradiation device, is called a beam angle or beam spread. The beam angle is an important metric in determining effective dosage received by a patient located at a given distance from the irradiation device, in medical applications. Also, the beam angle is used as an essential metric in determining illumination of a surface located at a given distance from the irradiation device in spatial lighting applications.

An improper beam angle of the irradiation can cause several problems such as improper dosage and ineffective treatment in therapeutic applications and insufficient lighting, glare problem, improper contrast, visual discomfort, and reflections on work surfaces (for example, computer screens) in spatial lighting applications. Conventionally available irradiation devices have had a fixed beam angle, therefore in applications where more than one beam angle of the irradiation is required, multiple irradiation devices of different corresponding beam angles had to be used.

However, with the advancement of technology in the irradiation devices, several patent documents, and irradiation devices have been introduced in the art to achieve variable beam angles, uniform electromagnetic radiation distribution in the visual environment and to overcome the aforementioned drawbacks. Even though these irradiation devices are capable of emitting radiation at variable beam angles, their construction has been rather complex, and their installation and operation are unlikely to be intuitive to an average user, and would rather require a significant amount of skill on the part of the user. For example, in one such irradiation device, to achieve the variation in the beam angle of the emitted beam of electromagnetic radiation from the irradiation device, a separate electromagnetic radiation cover is used as an external attachment, adding to the cost, the bulk and the skill required to maneuver the external attachment. Further, some of the irradiation devices use reflective optic members provided in the irradiation devices to control the beam angle of the emitted radiation, however, the use of the reflective optic members in the irradiation device makes the operation of the irradiation device more complex and cost-intensive.

Therefore, there is a need for an irradiation device that does not suffer from the aforementioned deficiencies.

Objects of the Invention

Some of the objects of the present invention are listed below:

It is an object of the present invention to provide an irradiation device which is capable of emitting electromagnetic radiation at variable beam angles;

It is another object of the present invention to provide an irradiation device which utilizes a plurality of lenses for adjusting the beam angle of the emitted radiation;

It is a further object of the present invention, that the plurality of lenses be selected on factors such as a particular beam angle, intensity of electromagnetic radiation, spot size in terms of length of the diameter of the spot created, a distance of the spot from the irradiation device, the intensity of the illumination at the location of the spot, a type of electromagnetic radiation source being used and other factors;

It is an additional object of the present invention to provide an irradiation device which is simple in construction and configuration;

It is an additional object of the present invention to provide an irradiation device that offers an economical way to obtain several beam angles from a single irradiation device; and It is a furthermore object of the present invention to provide an irradiation device that is convenient to use.

Other objects, features, advantages, and goals of the present invention will be better understood from the following detailed description taken in conjunction with the accompanying drawings.

SUMMARY

In accordance with an aspect of the present invention, there is provided an irradiation device capable of emitting electromagnetic radiation at variable beam angles, the irradiation device comprising a housing assembly including a longitudinal shell, the longitudinal shell having a first end and a second end, a first end cap assembly provided at the first end of the longitudinal shell, and a second end cap assembly provided at the second end of the longitudinal shell, a rotate and lock mechanism adapted to allow rotational adjustment of the longitudinal shell, a plurality of lenses provided along with the longitudinal shell, wherein each one of the plurality of lenses has a distinct set of optical characteristics when compared with other lenses of the plurality of lenses and a radiation source configured to emit electromagnetic radiation, provided within the longitudinal shell.

In one embodiment of the invention, the rotate and lock mechanism is constituted by a spring element and a contact element attached with the first end in the first end cap assembly, and a pair of meshing sets of teeth, wherein a first set of teeth of the pair, is provided at the second end of the longitudinal shell and a second set of teeth of the pair, is provided at an inner surface of the second end cap assembly.

In one embodiment of the invention, the radiation source is configured to be deactivated during the rotation of the longitudinal shell.

In one embodiment of the invention, the rotate and lock mechanism includes a first electrical actuator with a self-locking shaft, provided within the first end cap assembly.

In one embodiment of the invention, the radiation source is capable of rotating within the longitudinal shell.

In one embodiment of the invention, the irradiation device further comprises a second rotate and lock mechanism including a second electrical actuator with a second self-locking shaft, the second rotate and lock mechanism adapted to cause the rotational adjustment of the radiation source.

In one embodiment of the invention, the radiation source is configured to be deactivated during the rotation of the radiation source.

In one embodiment of the invention, the plurality of lenses includes a convex lens, a concave lens, and a Fresnel lens.

In one embodiment of the invention, the radiation source is configured to emit electromagnetic radiation in Ultra-Violet (UV), visible light, and Infrared (IR) wavelengths bands of the electromagnetic spectrum.

In one embodiment of the invention, the radiation source is configured to emit electromagnetic radiation in any one of a pulse mode and continuous mode.

In one embodiment of the invention, the radiation source includes one or more Light Emitting Diodes (LEDs).

In one embodiment of the invention, the one or more LEDs have been provided on an Organic LED (OLED) based flexible panel or an inorganic LED based flexible panel.

In one embodiment of the invention, the one or more LEDs are provided as a printable composition of micro-LEDs, printed on a substrate.

The following detailed description is illustrative in nature and is not intended to be in any way limiting. In addition to the illustrative aspects, embodiments, and features described above, further aspects, embodiments, and features will be apparent by reference to the following detailed description in conjunction with the accompanying drawings.

BRIEF DESCRIPTION OF ACCOMPANYING DRAWINGS

The accompanying drawings illustrate the best mode for carrying out the invention as presently contemplated and set forth hereinafter. The present invention may be more clearly understood from a consideration of the following detailed description of the preferred embodiments taken in conjunction with the accompanying drawings wherein like reference letters and numerals indicate the corresponding parts in various figures in the accompanying drawings, and in which.

Figure 1A:
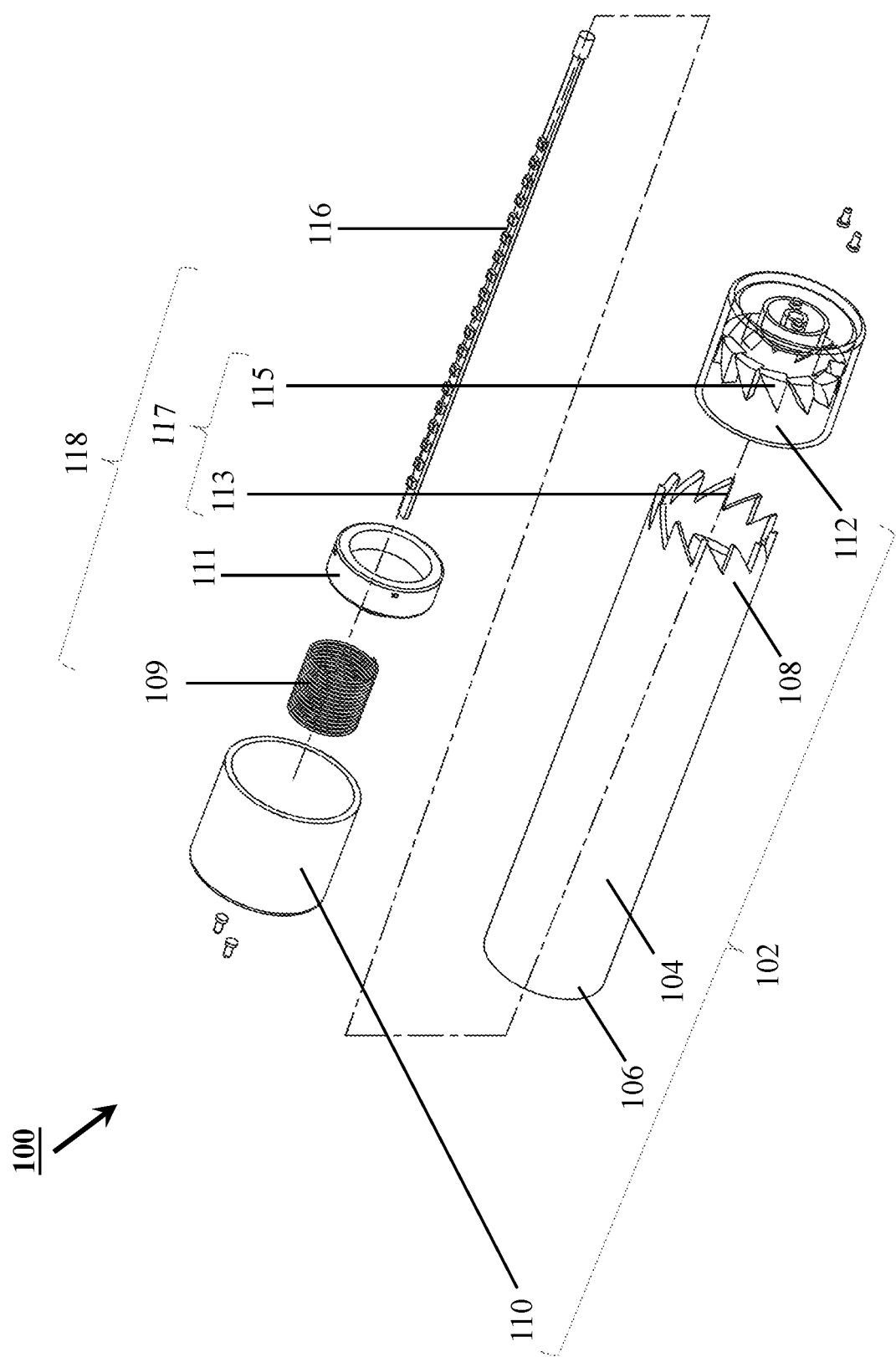
FIG. 1A illustrates an exploded view of an irradiation device capable of emitting electromagnetic radiation at variable beam angles, in accordance with an embodiment of the present invention.

While the present invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims and equivalents thereof.

DETAILED DESCRIPTION

Embodiments of the present invention disclosure will be described more fully hereinafter with reference to the accompanying drawings in which like numerals represent like elements throughout the figures, and in which example embodiments are shown.

The detailed description and the accompanying drawings illustrate the specific exemplary embodiments by which the disclosure may be practiced. These embodiments are described in detail to enable those skilled in the art to practice the invention illustrated in the disclosure. It is to be understood that other embodiments may be utilized, and other changes may be made, without departing from the spirit or scope of the present disclosure. The following detailed description is therefore not to be taken in a limiting sense, and the scope of the present invention disclosure is defined by the appended claims. Embodiments of the claims may, however, be embodied in many different forms and should not be construed as limited to the embodiments set forth herein.

The present invention provides an irradiation device that is capable of emitting electromagnetic radiation at variable beam angles. It is to be noted here that in the context of this specification, terms like "light", "radiation", "irradiation", "emission" and "illumination", etc. refer to electromagnetic radiation in frequency ranges varying from the Ultraviolet (UV) frequencies to Infrared (IR) frequencies and wavelength, wherein the range is inclusive of UV and IR frequencies and wavelengths. It is to be noted here that UV radiation can be categorized in several manners depending on respective wavelength ranges, all of which are envisaged to be under the scope of this invention. For example, UV radiation can be categorized as, Hydrogen Lyman-a (122-121 nm), Far UV (200-122 nm), Middle UV (300-200 nm), Near UV (400-300 nm). The UV radiation may also be categorized as UVA (400-315 nm), UVB (315-280 nm), and UVC (280-100 nm). Similarly, IR radiation may also be categorized into several categories according to respective wavelength ranges which are again envisaged to be within the scope of this invention. A commonly used subdivision scheme for IR radiation includes Near IR (0.75-1.4 µm), Short-Wavelength IR (1.4-3 µm), Mid-Wavelength IR (3-8 µm), Long-Wavelength IR (8-15 µm) and Far IR (15-1000 µm).

The irradiation device of the present invention has been envisaged to be embodied in a form factor of a linear Light Emitting Diode (LED) tube so that it can easily be mounted on readily available electrical fixtures and hence the invention does not necessitate any significant process architecture redesign and provide savings on capital investment. In that regard, several lenses with varying optical characteristics, such as thickness, focal length, concavity, color coating, and polarization, etc. may be provided along, on inner or outer surfaces of what would be a longitudinal shell of the linear LED tube. A radiation source may be provided within the longitudinal portion and variation in beam angles and other characteristics of the emitted electromagnetic radiation may be achieved through the relative rotation between the lenses and the radiation source. The radiation source in that regard may be monochromatic or may be capable of emitting radiation in a broad range of frequencies and wavelengths.

It is further envisaged, although not bindingly, that the radiation source may include Light Emitting Diodes (LEDs) for the invention, owing to power efficiencies achieved by the LEDs and rapid advancements in the field of LED technology which have made them available for several applications including indicator LEDs, lighting devices, treatment and automotive applications such as headlamps. The LEDs in that regard may be mounted on a Printed Circuit Board (PCB) through Surface Mounting Technology (SMT). SMT permits the creation of smaller PCB designs by allowing components to be placed closer together on the board that makes the device more lightweight and compact. The SMT process is faster to set up for production and requires less manufacturing cost than its counterpart, through-hole technology because it does not require the circuit board to be drilled for assembly.

In usage, it further envisaged that, through the relative rotation between the longitudinal shell and the radiation source, several ranges of beam angle may be achieved including spot (4-19 degrees), flood (20-35 degrees), wide flood (36-49 degrees) and very wide flood (50-120 degrees or more). The present irradiation device is envisaged to be applicable for both non-invasive therapeutic applications and spatial lighting purposes. However, certain design variations, such as a type, material or make of the radiation source, and emission characteristics of the emitted electromagnetic radiation may need to be altered to suit specific needs of an application, without departing from the scope of the invention. Referring to the figures, the invention will now be described in further detail.

FIG. 1A illustrates an exploded view of an irradiation device 100 capable of emitting electromagnetic radiation at variable beam angles, in accordance with an embodiment of the present invention. The irradiation device 100 as illustrated in FIG. 1A has been embodied in the form of a linear LED tube. The irradiation device 100 as shown in FIG. 1A includes a housing assembly 102 through which the light is emitted towards the surroundings. The housing assembly 102 includes a longitudinal shell 104 that may be made of glass, plastic, polycarbonate material, etc. It is further envisaged that the longitudinal shell 104 is at least partially transparent to allow electromagnetic radiation to pass through. The longitudinal shell 104 may also be made of nano plastic material that offers improved mechanical properties like hardness, stiffness, etc. over the over existing available material used in fluorescent lamps manufacturing. One of the several advantages of using nano plastic material is that the nano plastic material makes the longitudinal shell 104 highly resilient to damage, even when compared to the already robust polycarbonate and aluminum materials used in most of the lamps with a longitudinal or a linear form factor. However with the emergence of biopolymers for several applications, and materials of desired qualities being made increasingly available, the longitudinal shell 104 may also be constructed from bio-polymers or recycled conventional polymers for sustainability purposes.

The longitudinal shell 104 for this invention is envisaged to be a hollow body with a cross-section that may be circular, polygonal or elliptical, etc. depending upon specific applications. Also, the longitudinal shell 104 includes a first end 106 and a second end 108 at extremities of the longitudinal shell 104. The housing assembly 102 further includes a first end cap assembly 110 provided at the first end 106. Similarly, a second end cap assembly 112 provided at the second end 108. The irradiation device 100 further includes a radiation source 116 provided within the longitudinal shell 104. The radiation source 116 may be configured to emit electromagnetic radiation in Ultra-Violet (UV), visible light, and Infrared (IR) wavelengths bands of the electromagnetic spectrum, depending upon specific application of the irradiation device 100. In several embodiments of the invention, the radiation source 116 may include a plurality of Light Emitting Diodes (LEDs). The LEDs are characterized by their superior power efficiencies, smaller sizes, rapidity in switching, physical robustness, and longevity when compared with incandescent or fluorescent lamps. In that regard, the one or more LEDs may be through-hole type LEDs (generally used to produce electromagnetic radiations of red, green, yellow, blue and white colors), Surface Mount LEDs, Bi-color LEDs, Pulse Width Modulated RGB (Red-Green-Blue) LEDs, and high power LEDs, etc.

Materials used in the one or more LEDs may vary from one embodiment to another depending upon the frequency of radiation required. Different frequencies can be obtained from LEDs made from pure or doped semiconductor materials. Commonly used semiconductor materials include nitrides of Silicon, Gallium, Aluminum, and Boron, and Zinc Selenide, etc. in pure form or doped with elements such as Aluminum and Indium, etc. For example, red and amber colors are produced from Aluminum Indium Gallium Phosphide (AlGaInP) based compositions, while blue, green, and cyan use Indium Gallium Nitride based compositions. White light may be produced by mixing red, green, and blue lights in equal proportions, while varying proportions may be used for generating a wider color gamut. White and other colored lightings may also be produced using phosphor coatings such as Yttrium Aluminum Garnet (YAG) in combination with a blue LED to generate white light and Magnesium doped potassium fluorosilicate in combination with blue LED to generate red light. Additionally, near Ultra Violet (UV) LEDs may be combined with europium based phosphors to generate red and blue lights and copper and zinc doped zinc sulfide-based phosphor to generate green light.

In addition to conventional mineral-based LEDs, one or more LEDs may also be provided on an Organic LED (OLED) based flexible panel or an inorganic LED-based flexible panel. Such OLED panels may be generated by depositing organic semiconducting materials over Thin Film Transistor (TFT) based substrates. Further, discussion on generation of OLED panels can be found in *Bardsley*, J. N (2004), *"International OLED Technology Roadmap"*, *IEEE Journal of Selected Topics in Quantum Electronics*, Vol. 10, No. 1, that is included herein in its entirety, by reference. An exemplary description of flexible inorganic light-emitting diode strips can be found in granted U.S. Pat. No. 7,476,557 B2, titled "Roll-to-roll fabricated light sheet and encapsulated semiconductor circuit devices", which is included herein in its entirety, by reference.

In several embodiments, the one or more LEDs may also be micro-LEDs described through U.S. Pat. Nos. 8,809,126 B2, 8,846,457 B2, 8,852,467 B2, 8,415,879 B2, 8,877,101 B2, 9,018,833 B2 and their respective family members, assigned to *NthDegree Technologies Worldwide Inc.*, which are included herein by reference, in their entirety. The one or more LEDs, in that regard, may be provided as a printable composition of the micro-LEDs, printed on a substrate.

Further, it can be seen in FIG. 1A, the irradiation device 100 includes a rotate and lock mechanism 118 adapted to allow rotational adjustment of the longitudinal shell 104. The rotate and lock mechanism 118 is constituted by a spring element 109 and a contact element 111 attached with the first end 106 in the first end cap assembly 110. The contact element 111 is hollow on one side to receive the longitudinal shell 104 within and solid on another side that is in contact with the spring element 109. Also, a pair 117 of meshing sets of teeth, has been provided within the housing assembly 102, on the opposite side of the spring element 109. A first set of teeth 113 of the pair 117 is provided at the second end 108 of the longitudinal shell 104 and a second set of meshing teeth 115 of the pair 117, is provided at an inner surface of the second end cap assembly 112. It is to be noted here that the pair 117 of meshing sets of teeth may be designed to incorporate several least counts of angular adjustment of the longitudinal shell 104. For example, with the shift between one tooth of the second set 115 to another, an angular shift of 10 degrees of the longitudinal shell 104 may be effectuated. The least count, in this case, would, therefore, be 10 degrees. However, the rotate and lock mechanism 118 may be designed for different least counts such as 10, 20, 25, 30, 45, or 60 degrees, etc., depending upon specific applications.

Figure 1B:
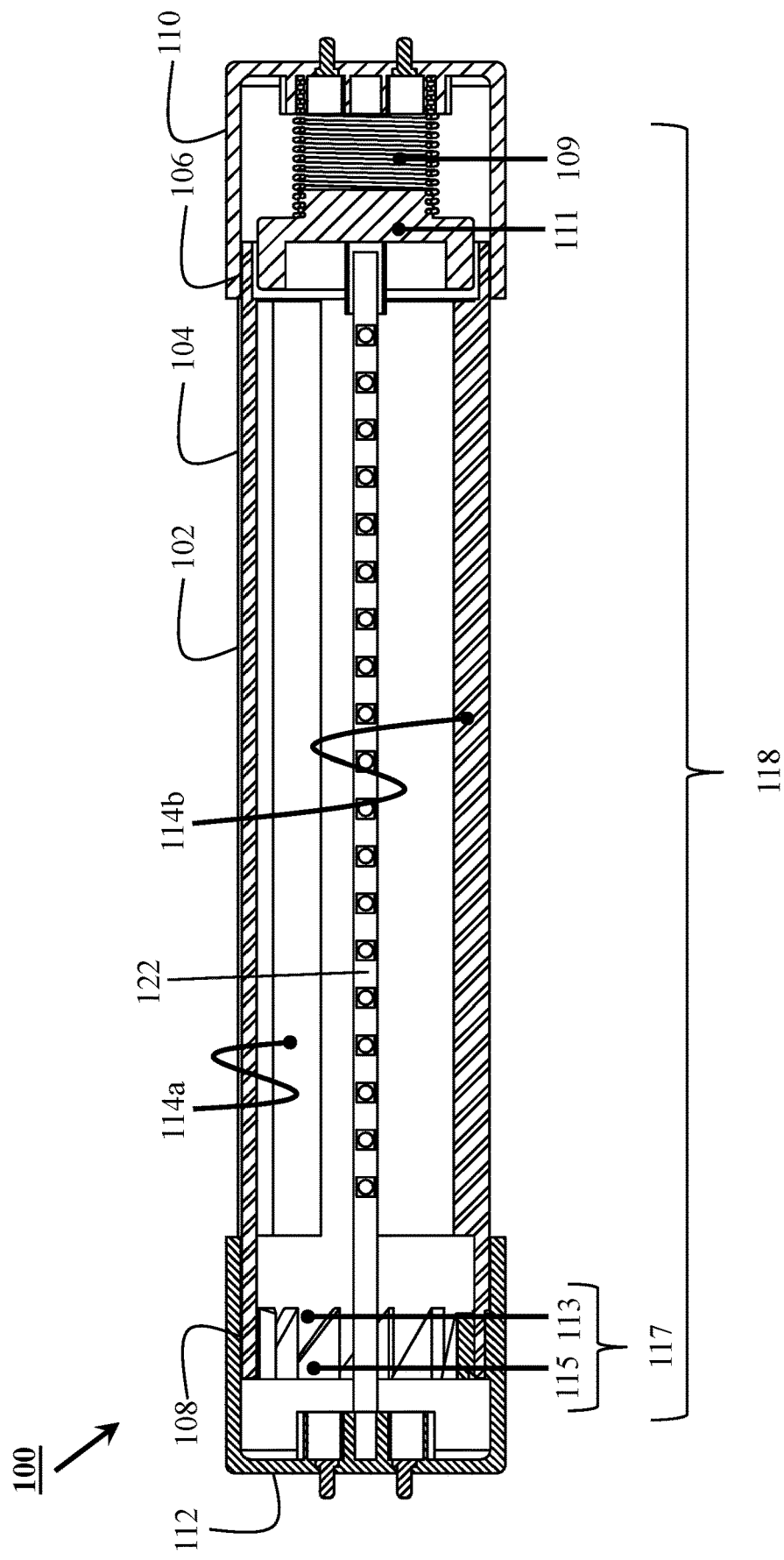
FIG. 1B illustrates a sectional view of the irradiation device of FIG. 1A, with a rotate and lock mechanism in an engaged position.

FIG. 1B illustrates a sectional view of the irradiation device 100 of FIG. 1A, with the rotate and lock mechanism 118 in an engaged position. In the engaged position, the spring element 109 is in the least compressed state thereby pushing the contact element 111 and therefore the longitudinal shell 104 against the second end cap assembly 112. The first set of meshing teeth 113 and the second set of meshing teeth 115 of the pair 117 are in a meshed state with respect to each other, thereby arresting any rotation of the longitudinal shell 104. The irradiation device 100 is further illustrated to include a plurality of lenses 114 (114a and 114b) provided along with the longitudinal shell 104. In that regard, the plurality of lenses 114 may be provided on one or more of an inner surface (such as lenses 114a and 114b) and an outer surface of the longitudinal shell 104. Also, anyone or more of the plurality of lenses 114 may be attached to the longitudinal shell 104, preferably on the outer surface, using an attachment means, depending upon the application of the irradiation device 100.

It is further envisaged that each one of the plurality of lenses 114 has a distinct set of optical characteristics from other lenses of the plurality of lenses 114. For example, the plurality of lenses 114 may have distinct shapes such as round, square and hexagonal, etc., opacity, additives, materials, coatings, and other such factors that may affect the radiation being received from the irradiation device 100. In that regards, the plurality of lenses 114 may be selected based on factors such as a particular beam angle, intensity, spot size in terms of length of the diameter of the spot created, distance of the spot from the irradiation device 100, the type of the radiation source 116, and other factors. Moreover, the plurality of lenses 114 may be suited to the specific construction of the radiation source 116 that might be used, for example for a single LED or an entire array of several LEDs arranged in a predetermined pattern, such as a one-dimensional strip or a two-dimensional board, where the radiation source 116 includes a plurality of LEDs. It is to be noted here that the one or more LEDs may or may not be available with pre-installed primary optics. The plurality of lenses 114 may include one or more concave, convex, Fresnel, or compound lenses. The plurality of lenses 114 in several embodiments may also include Total Internal Reflection (TIR) lenses that are mostly injection molded from a polymer material and utilize a refractive lens inside a reflector.

Figure 1C:
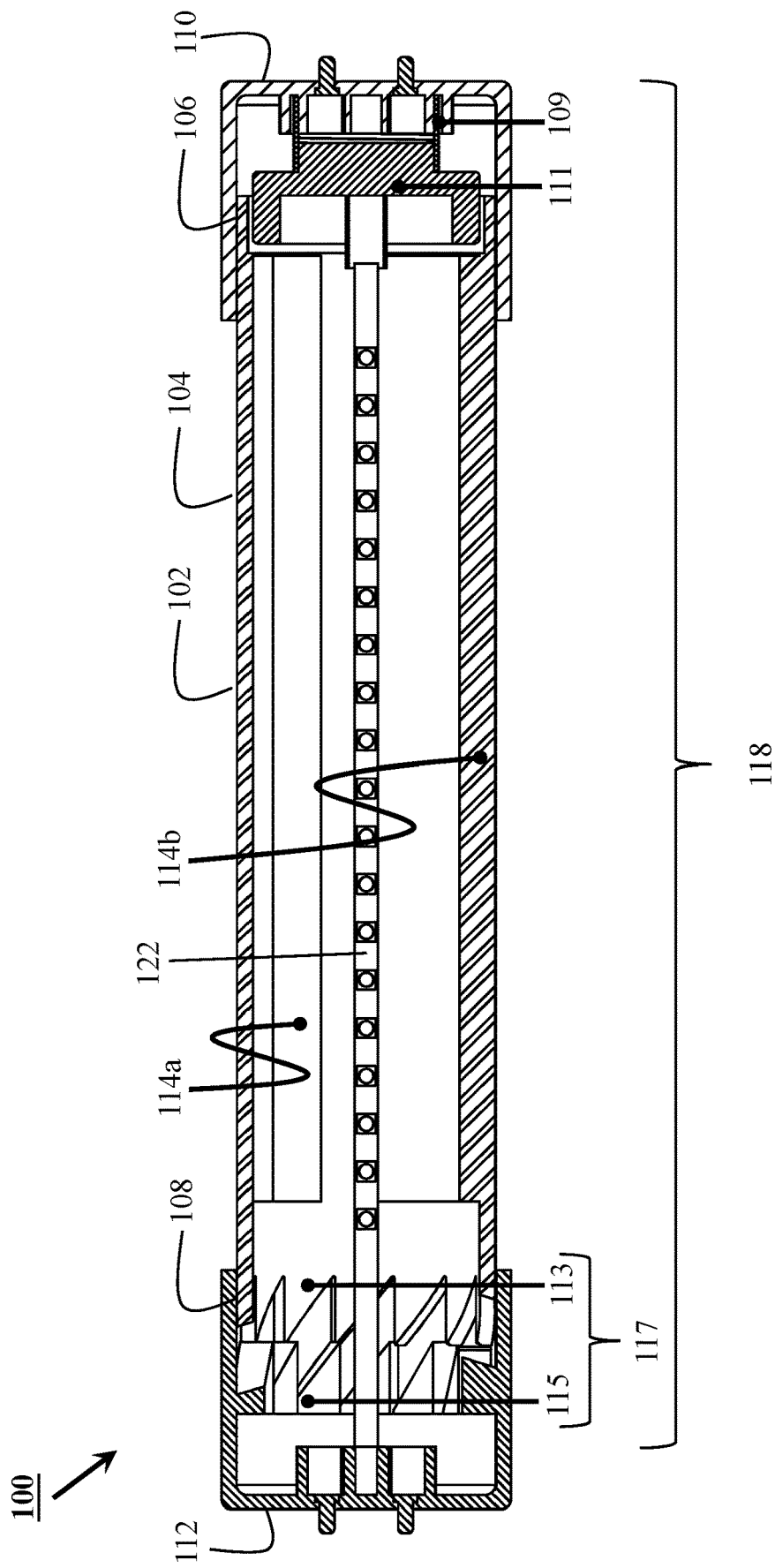
FIG. 1C illustrates a sectional view of the irradiation device of FIG. 1A, with the rotate and lock mechanism in a disengaged position.

FIG. 1C illustrates a sectional view of the irradiation device 100 of FIG. 1A, with the rotate and lock mechanism 118 in a disengaged position. In the disengaged position, the spring element 109 is in a maximum compressed state thereby releasing the contact element 111 and therefore the longitudinal shell 104 from the second end cap assembly 112. The first set of meshing teeth 113 and the second set of meshing teeth 115 of the pair 117 are unmeshed with respect to each other, thereby allowing rotational adjustment of the longitudinal shell 104. The longitudinal shell 104 may then be rotated to facilitate alignment of a predetermined lens of the plurality of lenses 114 with the radiation source 116 to modify emission characteristics, including the beam angle, of the electromagnetic radiation emitted by the irradiation device 100.

Figure 2:
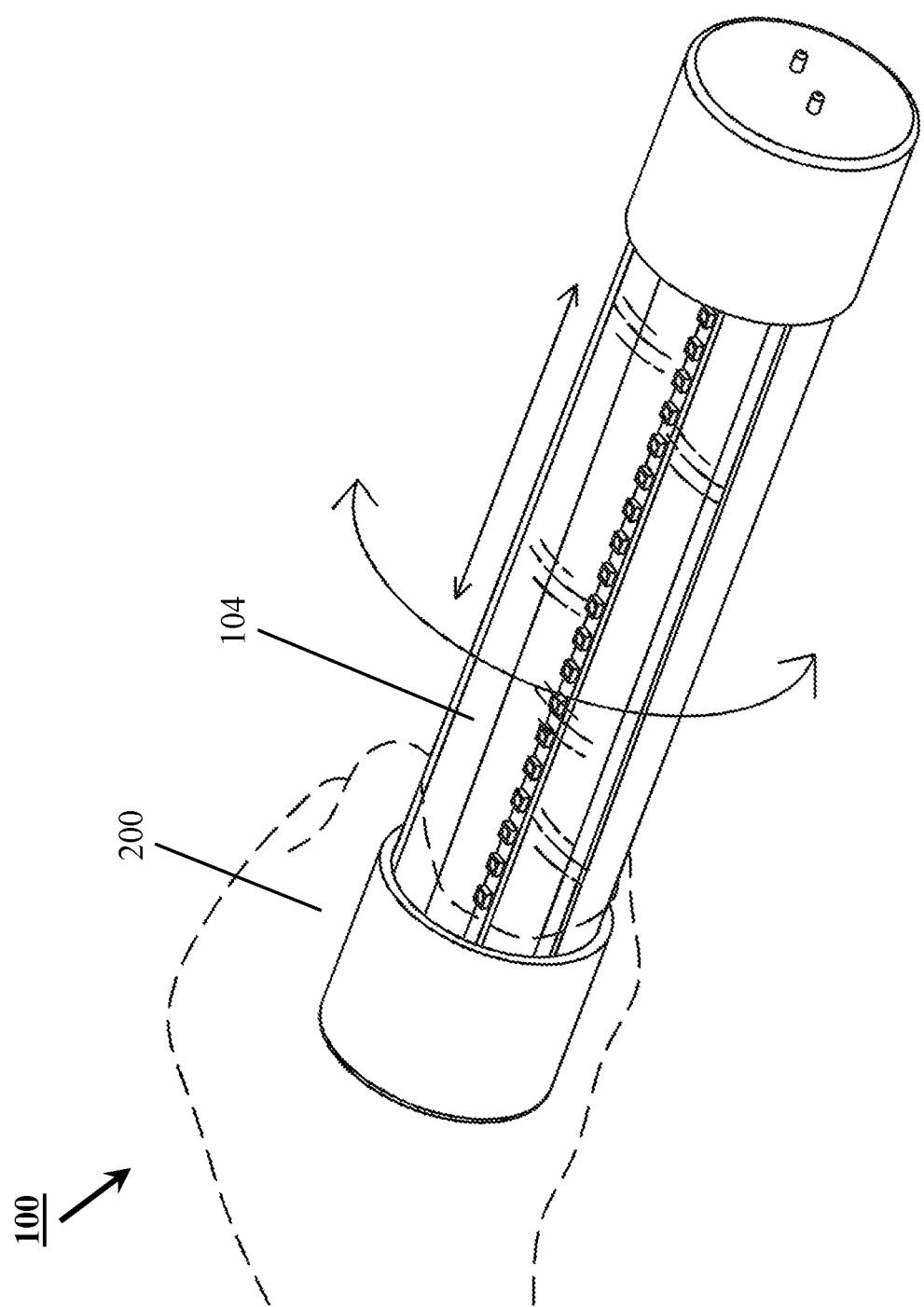
FIG. 2 illustrates a visual representation of a rotational adjustment of a longitudinal shell of the irradiation device of FIG. 1A.

FIG. 2 illustrates a visual representation of the rotational adjustment of the longitudinal shell 104 of the irradiation device 100 of FIG. 1A. As depicted in FIG. 2, an operator 200 may be able to hold the longitudinal shell 104 and push it backward towards the first end cap assembly 110, thereby compressing the spring element 109. This allows the pair 117 of the first set of meshing teeth 113 and the second set of meshing teeth 115, to disengage, in the second end cap assembly 112, thereby allowing rotational adjustment of the longitudinal shell 104. In addition, special contact-based electrically conducting terminals may be provided between the first 113 and the respective second 115 sets of meshing teeth, to ensure that power supply to the radiation source 116 is only available when the pair 117 is in meshed state and the power supply to the radiation source 116 may be cut-off when the first 113 and the respective second 115 sets of meshing teeth are no longer in contact with each other. This is both a safety measure to prevent the operator 200 from accidental exposure to potentially harmful radiation, of the operator 200 during angular adjustment of the longitudinal shell 104 and to save electrical power as the radiation source 116 need not necessarily be activated during the angular adjustment of the longitudinal shell 104.

Figure 3:
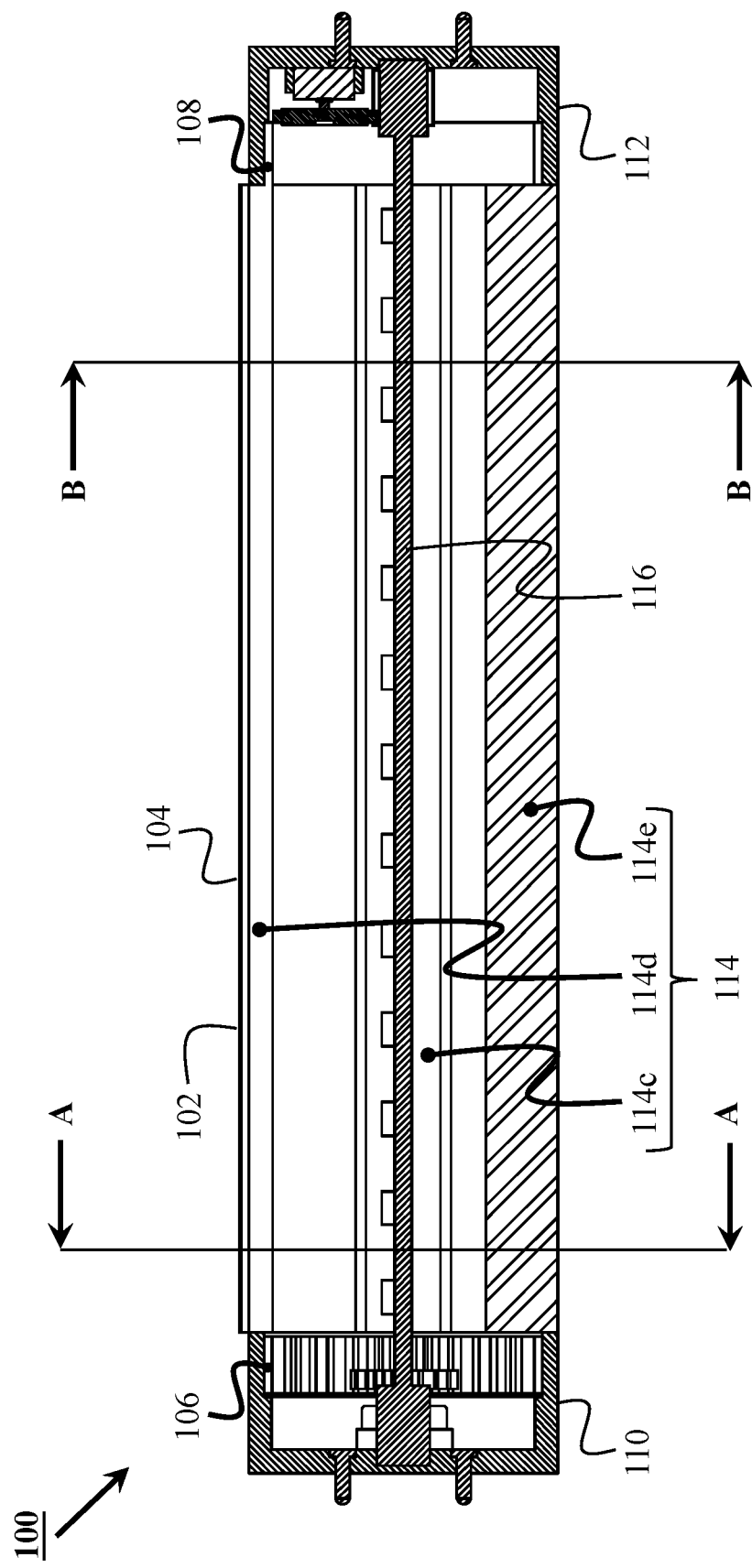
FIG. 3 illustrates a sectional view of the irradiation device capable of emitting electromagnetic radiation at variable beam angles, in accordance with another embodiment of the present invention.

FIG. 3 illustrates a sectional view of the irradiation device 100 capable of emitting electromagnetic radiation at variable beam angles, in accordance with another embodiment of the present invention. It can be seen in FIG. 3, that the irradiation device 100, in this embodiment includes three lenses 114 (114c, 114d, and 114e), as against two (114a, 114b) depicted in the previous embodiment of FIG. 1A. Although, the invention is not limited to a specific number for the plurality of lenses 114 or specific construction of the plurality of lenses 114.

Figure 4A:
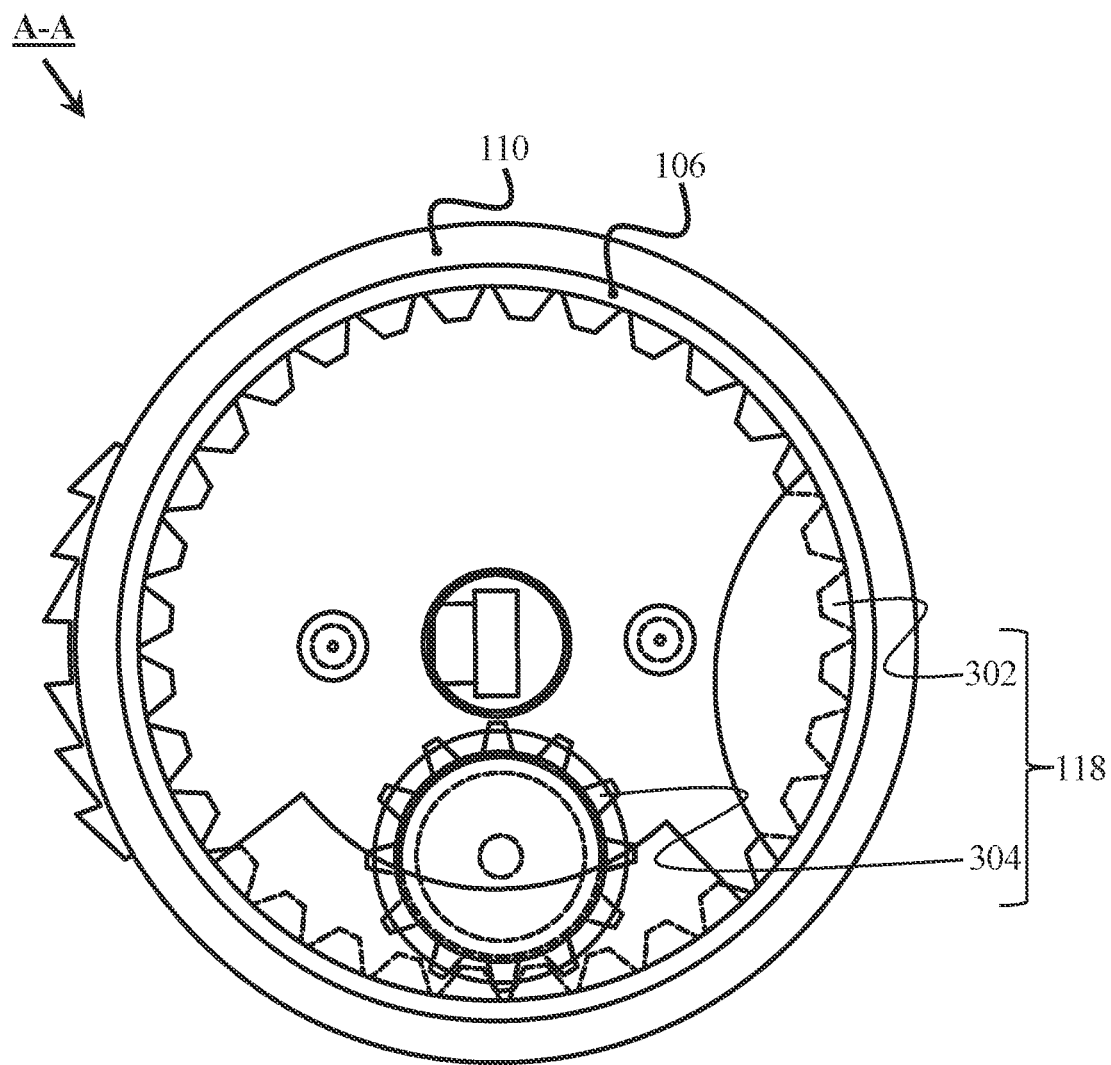
FIG. 4A illustrates a sectional view of the irradiation device of FIG. 3, sectioned along a plane A-A.

FIG. 4A illustrates a sectional view of the irradiation device 100 of FIG. 3, sectioned along a plane A-A. As illustrated in FIG. 4A, the rotate and lock mechanism 118 is constituted by meshing gear teeth sets 302 and 304, wherein a first set of gear teeth 302 has been provided along an inner surface of the first end 106 of the longitudinal shell 104. Further, a second set of gear teeth 304 has been provided through a gear located within the first end cap assembly 110. The rotate and lock mechanism 118 is adapted to cause rotation of the longitudinal shell 104 when actuated by an actuator. In several embodiments of the present invention, the radiation source 116 is capable of rotating within the longitudinal shell 104.

Figure 4B:
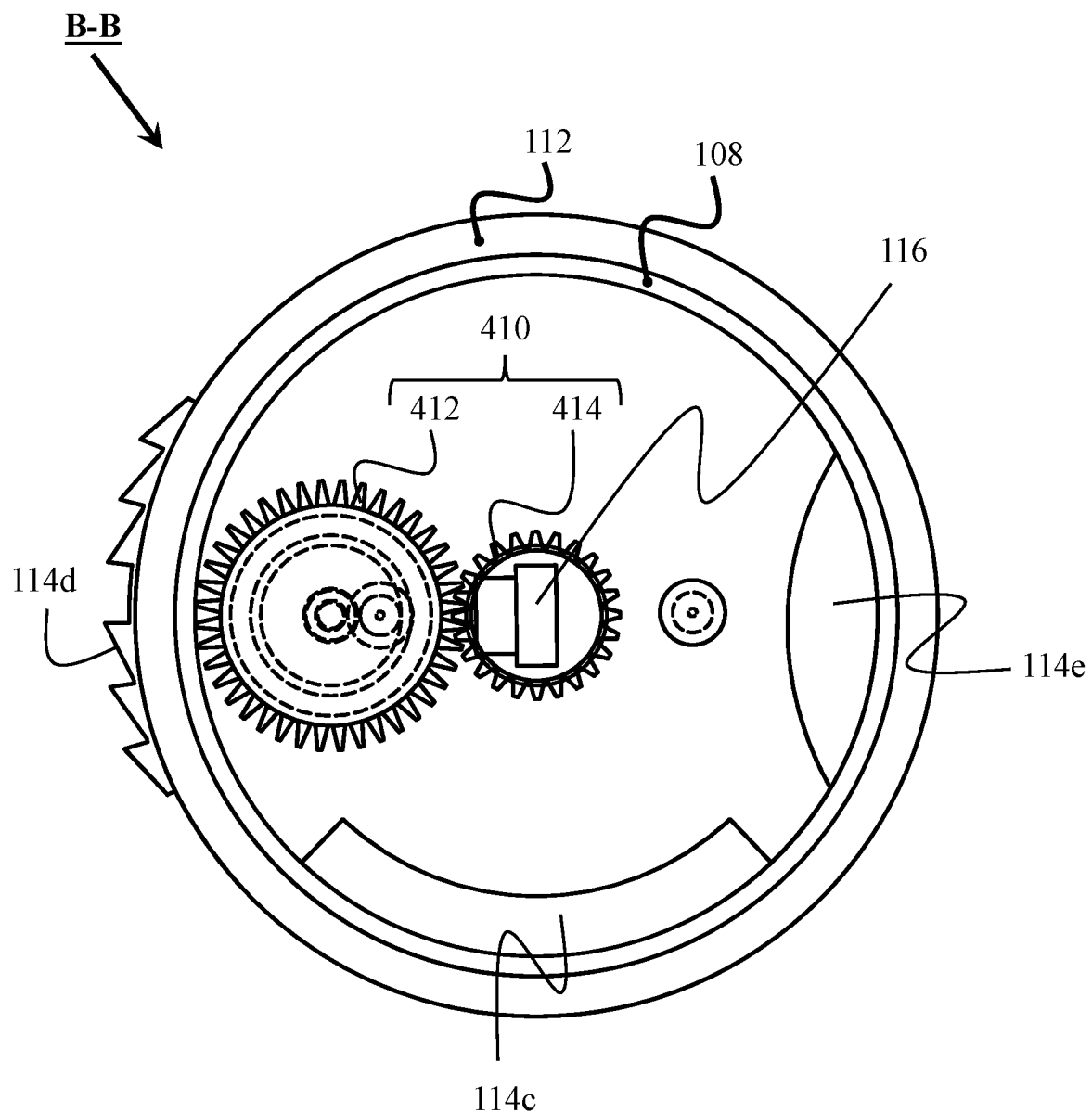
FIG. 4B illustrates a sectional view of the irradiation device of FIG. 3, sectioned along a plane B-B.

FIG. 4B illustrates a sectional view of the irradiation device 100 of FIG. 3, sectioned along a plane B-B. As illustrates in FIG. 4B, the radiation source 116 is also capable of rotating within the longitudinal shell 104, through meshing gear teeth sets 412 and 414 of a second rotate and lock mechanism 410. Further, the second rotate and lock mechanism 410 has been provided within the second end cap assembly 112. However, a person skilled in the art would appreciate that the locations of the rotate and lock mechanism 118 and the second rotate and lock mechanism 410 are interchangeable or both may be located at any one end of the longitudinal shell 104.

Figure 5:
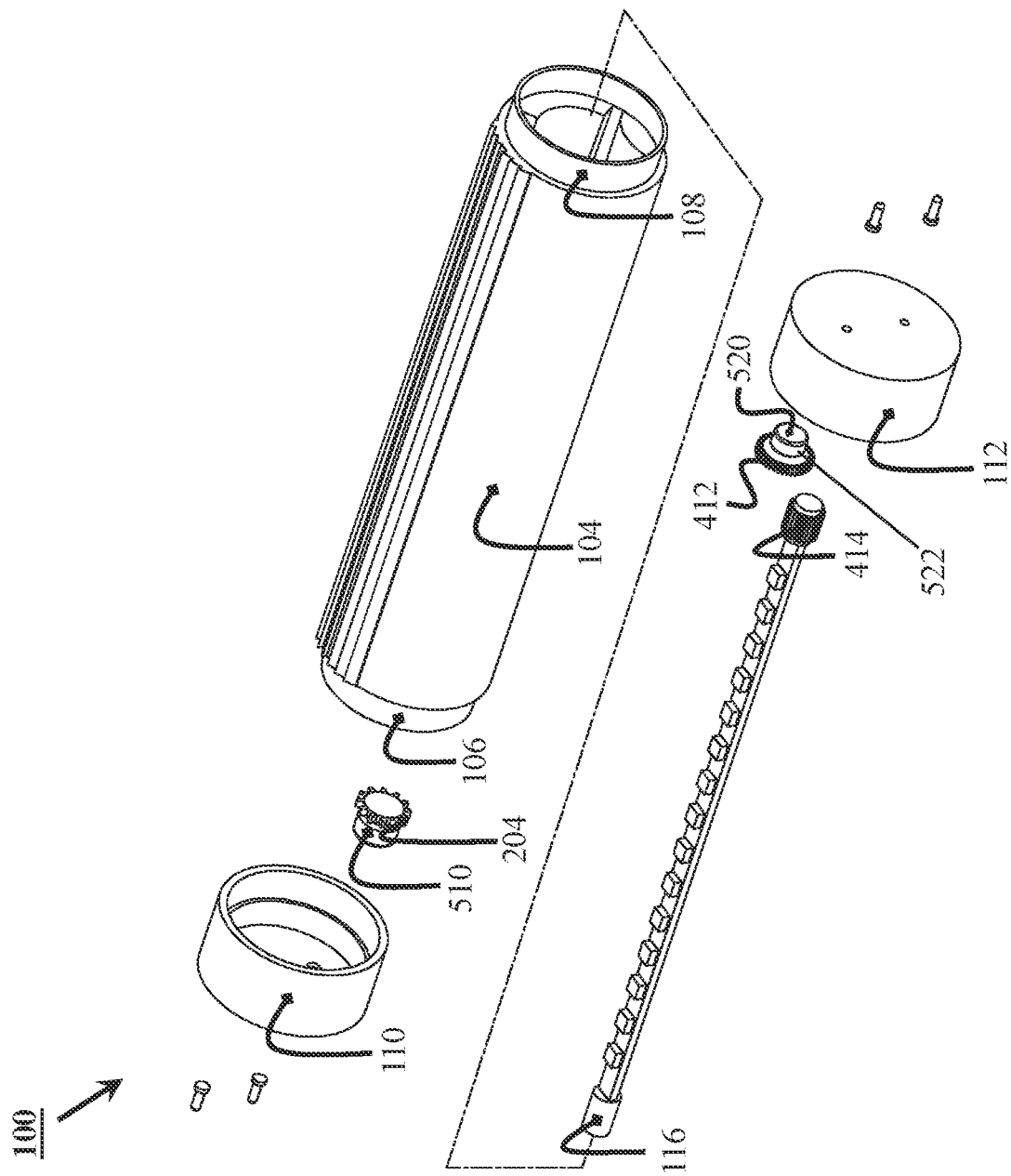
FIG. 5 illustrates an exploded view of the irradiation device of FIG. 3.

FIG. 5 illustrates an exploded view of the irradiation device 100 of FIG. 3. As illustrated in FIG. 5, the rotate and lock mechanism 118 includes a first electrical actuator 510 adapted to cause the rotation of the second set of gear teeth 204. In that regard, the first electrical actuator 510 may be an AC motor, a DC motor, a servo motor, a stepper motor, or the like. Also, a second electrical actuator 520 is adapted to cause the rotation of the radiation source 116 through the rotation of the gear teeth set 414 of the second rotate and lock mechanism 410. Similar to the first electrical actuator 510, the second electrical actuator may also be an AC motor, a DC motor, a servo motor, a stepper motor, or the like. However, to enable rotation of the radiation source 116 instead of the longitudinal shell 104, it would be advantageous from the utilization point of view that the rotation of the longitudinal shell 104 is prevented.

Following the determination of the direction of the radiation source 116, the longitudinal shell 104 may be allowed to rotate for alignment of the radiation source 116 with any predetermined lens of the plurality of lenses 114. Following the alignment of the radiation source 116 with any one of the plurality of lenses 114, the longitudinal shell 104 may be desired to be locked again. Additionally, even in scenarios where the longitudinal shell 104 alone is being rotated in place of the radiation source 116, it would be advantageous to lock the rotation of the longitudinal shell 104, once the adjustment has been performed, to ensure any accidental movement or misalignment of the radiation source 116 with any one of the plurality of lenses 114.

Therefore, it is further envisaged that in several embodiments, the first electrical actuator 510 may be a DC motor with a self-locking shaft that is locked in its position until the current is supplied to the first electrical actuator 510. The self-locking shaft of the first electrical actuator 510 would be capable of arresting the rotation of the longitudinal shell 104. It is also envisaged that the second electrical actuator 520 may also be a DC motor with a self-locking shaft that is locked in its position until the current is supplied to the second electrical actuator 520. The self-locking shaft of the second electrical actuator 520 would then be capable of arresting the rotation of the radiation source 116. The self-locking shafts of the first electrical actuator 510 and the second electrical actuator 520 may include self-locking arrangements such as worm and worm shaft type, solenoid brake type, or any other self-locking shaft arrangements known in the art.

Figure 6:
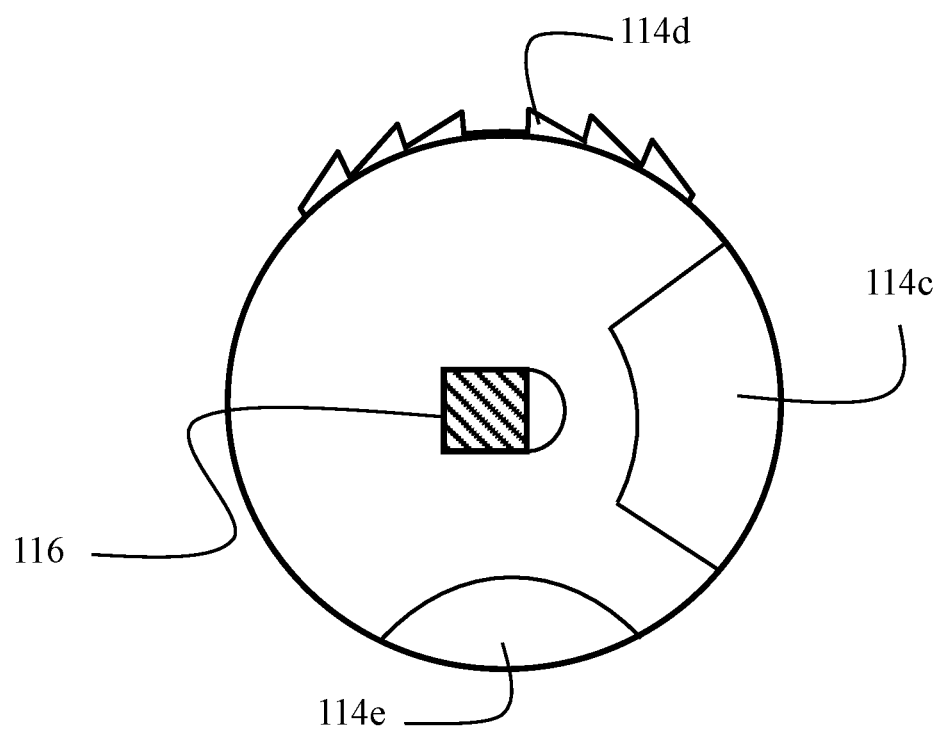
FIG. 6 illustrates a cross-sectional view of the irradiation device of FIG. 3.

FIG. 6 illustrates a cross-sectional view of the irradiation device 100 of FIG. 3. The plurality of lenses 114 (114c, 114d, and 114e) such as concave, Fresnel, and convex lens are provided along with the longitudinal shell 104 of the irradiation device 100 as shown in FIG. 6. The concave lens 114c and the convex lens 114e have been provided along the inner surface of the longitudinal shell 104, while the Fresnel lens 114d has been provided along the outer surface of the longitudinal shell 104. However, the invention is not limited to the aforementioned concave, convex, and Fresnel lens apart from them, different types of lenses having distinct focal length can be used for the invention.

In use, a user may rotate the longitudinal shell 104 of the irradiation device 100 by actuating, either remotely or through a contact-based switch, the first electrical actuator 510. Due to the rotational movement of longitudinal shell 104, the plurality of lenses 114 provided along with the longitudinal shell 104 also rotate, resulting in the beam angle adjustment of the radiation emitted by the radiation source 116, when one of the plurality of lenses 114 aligns with the radiation source 116. Alternately, the user may actuate the second electrical actuator 520, thus causing the rotation of the radiation source 116 to align with a predetermined lens of the plurality of lenses 114. In such a scenario, not only variations in beam angles would be achieved, but the beam direction will also change with the rotation of the radiation source 116.

It is further envisaged, that during the rotation of the longitudinal shell 104 or the radiation source 116, special provisions may be made available to ensure that the radiation source 116 is inactive during the adjustment of the beam angle and other optical characteristics, to ensure power savings and undesirable light glare problems caused to an operator. For example, motion sensors may be installed on the longitudinal shell 104 and the radiation source 116, that may detect the rotation of the longitudinal shell 104 and the radiation source 116 and cause the deactivation of the radiation source 116. The deactivation of the radiation source 116 may also be facilitated through an electromechanical or solid-state switch that may be operated either automatically based on motion sensor feedback or manually by the operator.

The irradiation device 100 has been designed to operate both as a therapeutic device for non-invasive radiation treatment for conditions such as skin acne and aging, muscle spasms and inflammations and in some cases benign or malignant lesions and as an artificial lighting device in spatial lighting applications. In that regard, during utilization of the irradiation device 100 for therapeutic applications, the key factors that may affect the efficacy of the treatment include wavelengths, the power density of irradiation, time of exposure, distance of the affected area from the irradiation device 100 and mode of operation of the radiation source 116. In that regard, the radiation source 116 may be configured to operate in pulsed or continuous mode. In that regard, for input current of (I mA) and applied voltage of (V Volts), the Input Power ($P_I$) being supplied to the irradiation device 100 would be given by equation (1).

$$P_I = V \times I \text{ mW} \tag{1}$$

For the overall efficiency ($\eta$) of the irradiation device 100, the Output Power ($P_O$) would be given by equation (2).

$$P_o = \eta \times P_I \text{ mW} \tag{2}$$

The area (A) being effectively irradiated by the irradiation device 100, with a beam angle ($\theta$), for a subject standing at a distance (d cm) would be given by equation (3).

$$A = \pi \times \left( d \times \tan\left(\frac{\theta}{2}\right) \right)^2 \text{ cm}^2 \tag{3}$$

Hence, the Power Density ($P_d$) being received at the distance (d) would be given by the equation (4).

$$P_d = K \times \frac{P_O}{A} \text{ mW}/\text{cm}^2 \tag{4}$$

Where K is the correction factor for accounting for the entire beam spread that will be greater than the beam angle. The correction factor 'K' may be empirically determined during the calibration of the irradiation device 100. Therefore, the dosage (D) and total irradiant energy ($E_a$) being absorbed by the subject, receiving treatment for a time period (T seconds) would be given by equations (5) and (6), respectively.

$$D = P_d \times T \text{ mJ}/\text{cm}^2 \tag{5}$$

$$E_a = D \times A \text{ mJ} \tag{6}$$

From equations (1) to (6) it can thus be inferred that for a given design of the irradiation device 100, the treatment received by the subject individual may be varied by varying parameters such as the input current, applied voltage, beam angle of the irradiation, distance of the subject from the irradiation device and treatment time, etc. For example, an effective dose for wound healing is 90 J/cm². It has to be further noted that the value of input current, applied voltage, and construction of the radiation source 116 (for example be it laser or LEDs) will also be dictated by other factors such as type of condition (for example, acne, deep wounds, and lesions, etc.) and type of radiation output (for example, blue light, UV radiation, red light or IR radiation) suited for that condition.

Alternately, during utilization of the irradiation device 100 as an artificial lighting device for spatial lighting, a different set of characteristics come into play. Moreover, it is to be noted that in such applications the irradiation device 100 would most likely be emitting radiation in form of the wide spectrum visible light and therefore the efficacy of the irradiation device 100 would be evaluated differently than as described through equations (1) to (6). The key characteristics in the application of the irradiation device 100 include angular span, beam angle, apex angle, a distance of a surface being illuminated from the irradiation device 100, luminous intensity and luminous flux being emitted. For a surface at a distance (d) cm from the irradiation device 100, emitting visible light at a beam angle ($\theta$), the apex angle ($\alpha$) would be determined from equation (7) and angular span ($\sigma$) would be determined from equation (8).

$$\alpha = 2\theta \tag{7}$$

$$\sigma = 2\pi \left(1 - \cos\left(\frac{\alpha}{2}\right)\right) \text{ steradians} \tag{8}$$

For a given luminous intensity (C candela), the luminous flux (L) would be determined from equation (9).

$$L = C \times \sigma \text{ lumens} \tag{9}$$

Thus, the illumination of the surface, also known as the lux value at the surface may be determined by dividing the luminous flux (L) with the area (A) determined from equation (3). The lux value (l) is thus given by equation (10).

$$l = \frac{L}{A} \text{ lumens}/\text{cm}^2 \tag{10}$$

The lux value (l) is generally the value that is measured by light meters. Also, it can be seen from equation (10) and (3) that the lux value, therefore, depends on the beam angle and the distance of the surface from the irradiation device 100.

Figure 7A:
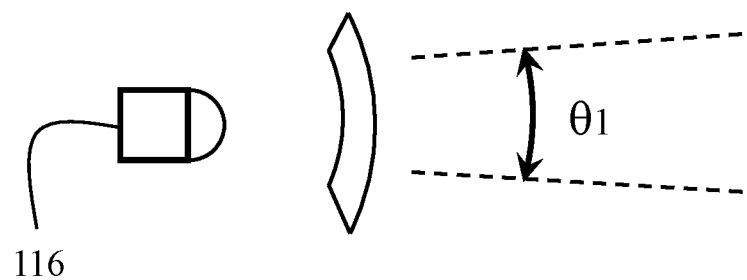
FIG. 7A illustrates a narrow beam angle of an irradiation device using a first lens, in accordance with another embodiment of the present invention.

FIG. 7A illustrates a narrow beam angle ($\theta_1$) of an irradiation device 100 using a first lens having a relatively long focal length, in accordance with another embodiment of the present invention. The first lens used in this embodiment when aligned with the radiation source 116 emits light at the narrow beam angle (5 to 20 degree).

Figure 7B:
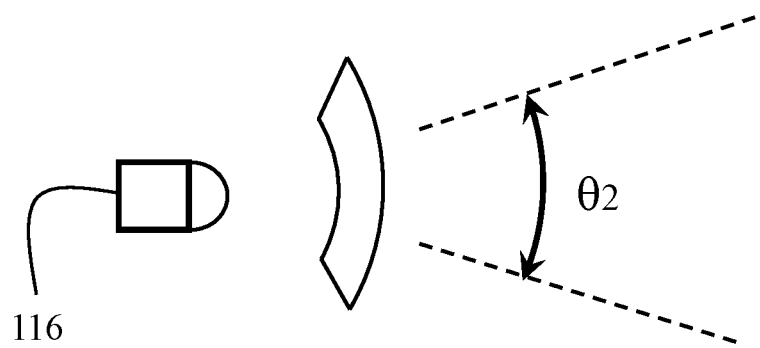
FIG. 7B illustrates a flood beam angle of the irradiation device using a second lens of the irradiation device of FIG. 7A.

FIG. 7B illustrates a flood beam angle ($\theta_2$) of the irradiation device 100 using a second lens having a relatively shorter focal length when compared with the first lens. The second lens used in this embodiment when aligned with the radiation source 116 emits light at the flood beam angle (20 to 50 degrees).

Figure 7C:
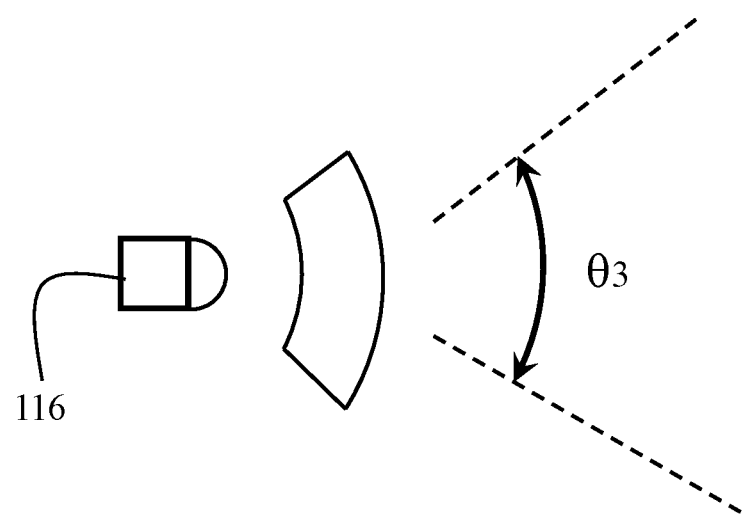
FIG. 7C illustrates a wide beam angle of the irradiation device using a third lens of the irradiation device of FIG. 7A.

FIG. 7C illustrates a wide beam angle ($\theta_3$) of the irradiation device 100 using a third lens having an even shorter focal length when compared with the second lens. The third lens used in this embodiment when aligned with the radiation source 116 emits light at a broader beam angle (more than 50 degrees).

The construction of the irradiation device as described above is not only economical from a manufacturing point of view, but the embodiment of the irradiation device in form of a linear LED tube would allow the irradiation device to be mounted in readily available electrical fixtures. This would allow both savings in time and effort that would have been required in the redesign of the electrical fixtures but also savings in capital investment that would have been incurred in the purchase and installation of such fixtures.

EXAMPLE 1

As an example, for an irradiation device 100 rated at luminous intensity (C) of 1000 candela at an apex angle (α) of 70 degrees, the beam angle (θ), angular span (σ) and luminous flux (L) would be determined as below:

$$\theta = \frac{70}{2} = 35°$$

$$\sigma = 2\pi\left(1 - \cos\left(\frac{70}{2}\right)\right) = 1.136 \text{ steradians}$$

$$L = 1.136 \times 1000 = 1136 \text{ lumens}$$

For a surface that is at a distance of 1 m or 100 cm from the irradiation device 100, the illumination of the surface or lux value (1) would be determined as follows:

$$A = \pi \times \left(100 \times \tan\frac{35}{2}\right)^2 = 3123.2 \text{ cm}^2$$

$$l = \frac{1136}{3123.2} = 0.364 \text{ lumens/cm}^2$$

Although specific embodiments and certain structural arrangements have been illustrated and described herein, it will be clear to those skilled in the art that various other modifications and embodiments may be made incorporating the spirit and scope of the underlying inventive concepts and that the same is not limited to the particular methods and structure herein shown and described except in so far as determined by the scope of the appended claims.

The invention claimed is:

1. An irradiation device capable of emitting electromagnetic radiation at variable beam angles, the irradiation device comprising:
   a housing assembly including:
      a longitudinal shell, the longitudinal shell having a first end and a second end, a first end cap assembly provided at the first end of the longitudinal shell, and a second end cap assembly provided at the second end of the longitudinal shell,
      a rotate and lock mechanism adapted to allow rotational adjustment of the longitudinal shell,
      a plurality of lenses provided along with the longitudinal shell, wherein each one of the plurality of lenses has a distinct set of optical characteristics when compared with other lenses of the plurality offenses, and
      a radiation source configured to emit electromagnetic radiation, provided within the longitudinal shell, wherein the radiation source includes one or more Light Emitting Diodes (LEDs);
   wherein the rotate and lock mechanism is constituted by a spring element and a contact element attached with the first end in the first end cap assembly, and a pair of meshing sets of teeth, wherein a first set of teeth of the pair is provided at the second end of the longitudinal shell and a second set of teeth of the pair is provided at an inner surface of the second end cap assembly,
   wherein contact based electrically conducting terminals are provided between the first and the respective second sets of teeth to ensure that the power supply to the radiation source is only available when the pair of sets of teeth are in meshed state and power supply to the radiation source is cut-off when the first and the respective second sets of teeth are no longer in contact with each other.

2. The irradiation device as claimed in claim 1, wherein the plurality of lenses includes a convex lens, a concave lens, and a Fresnel lens.

3. The irradiation device as claimed in claim 1, wherein the radiation source is configured to emit the electromagnetic radiation in Ultra-Violet (UV), visible light, and Infrared (IR) wavelength bands of the electromagnetic spectrum.

4. The irradiation device as claimed in claim 1, wherein the radiation source is configured to emit the electromagnetic radiation in any one of a pulse mode and continuous mode.

5. The irradiation device as claimed in claim 1, wherein the one or more LEDs have been provided on an Organic LED (OLED) based flexible panel or an inorganic LED based flexible panel.

6. The irradiation device as claimed in claimed in claim 1, wherein the one or more LEDs are provided as a printable composition of micro-LEDs, printed on a substrate.

* * * * *